United States Patent
Kvamme

(10) Patent No.: US 7,292,393 B2
(45) Date of Patent: Nov. 6, 2007

(54) VARIABLE ILLUMINATOR AND SPECKLE BUSTER APPARATUS

(75) Inventor: Damon F. Kvamme, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 153 days.

(21) Appl. No.: 11/055,893

(22) Filed: Feb. 11, 2005

(65) Prior Publication Data

US 2006/0152810 A1    Jul. 13, 2006

Related U.S. Application Data

(60) Provisional application No. 60/643,618, filed on Jan. 12, 2005.

(51) Int. Cl.
G02B 27/44    (2006.01)

(52) U.S. Cl. ..................... 359/566; 359/558
(58) Field of Classification Search ............... None
See application file for complete search history.

(56) References Cited

U.S. PATENT DOCUMENTS

| | | | |
|---|---|---|---|
| 4,669,885 A | 6/1987 | Ina | 356/443 |
| 4,732,473 A | 3/1988 | Bille et al. | 356/237.5 |
| 5,264,912 A | 11/1993 | Vaught et al. | 356/237.5 |
| 5,270,850 A | 12/1993 | Mochizuki et al. | 359/206 |
| 5,541,731 A | 7/1996 | Freedenberg et al. | 356/496 |
| 5,623,340 A | 4/1997 | Yamamoto et al. | 356/237.4 |
| 5,646,765 A | 7/1997 | Laakmann et al. | 359/202 |
| 5,680,588 A | 10/1997 | Gortych et al. | 716/19 |

(Continued)

OTHER PUBLICATIONS

"Core Competencies", Digitial Optics Corporation, www.doc.com/tech_overview.asp, downloaded Oct. 16, 2003.
Douglas Goodman, "Optics of Photo Lithography", Optical Society of America, OptCon, Santa Clara, CA 1988, pp. 112-117.
Conant et al., "A Flat High-Frequency Scanning Micromirror", Berkeley Sensor & Actuator Center, University of Cliforina, Berkeley, Berkeley, CA 94720-1774, p. 1-4.
Naulleau et al., "Static Microfield Printing at the Advanced Light Source with the ETS Set-2 Optic", Emerging Lithographic Technologies VI, Proceedings of SPIE vol. 4688, p. 64-71, (2002).

(Continued)

Primary Examiner—Arnel Lavarias
(74) Attorney, Agent, or Firm—Beyer Weaver LLP

(57) ABSTRACT

Disclosed is an apparatus for illuminating a sample. In one embodiment, this apparatus includes a laser for outputting an incident laser beam towards a sample and a first diffractive element having a plurality of diffraction pattern portions. The first diffractive element is movable so that each of its diffraction pattern portions can be selectively positioned in the incident beam's path and the diffraction pattern portions of the first diffractive element are designed to cause the incident beam to have different spatial illumination profiles at a pupil plane of the incident beam while reducing effects caused by the incident beam's coherence. The apparatus further includes an illumination profile element configured to spatially distribute light at an illumination plane of the incident beam and a plurality of illumination optical elements for directing the incident beam towards the sample.

20 Claims, 6 Drawing Sheets

U.S. PATENT DOCUMENTS

| | | | |
|---|---|---|---|
| 5,838,433 A | 11/1998 | Hagiwara | 356/364 |
| 5,847,400 A | 12/1998 | Kain et al. | 250/458.1 |
| 5,847,746 A | 12/1998 | Takahashi | 347/241 |
| 6,248,988 B1 | 6/2001 | Krantz | 250/201.3 |
| 6,556,290 B2 | 4/2003 | Maeda et al. | 356/237.2 |
| 6,621,571 B1 | 9/2003 | Maeda et al. | 356/237.5 |
| 6,882,417 B2 | 4/2005 | Goldberg et al. | 356/237.4 |
| 2004/0125459 A1* | 7/2004 | Tanitsu et al. | 359/619 |

OTHER PUBLICATIONS

Adam Fedor, "Binary Optic Diffuser Design", Digital Optics Corp., pp. 1-11, www.docs.com, printed Oct. 16, 2003.

Lincoln Laser, "Data Sheet Polygonal Mirrors Diamond Machined Convertionally Polished", printed Oct. 16, 2003 http://www.lincolnlaser.com/products/pdf_mirrors.pdf.

Roncone et al., Patent Application entitled "Optical Compensation in High Numberical Aperture Photomask Inspection Systems for Inspecting Photomasks through Thick Pellicles", U.S. Appl. No. 10/401,614, filed Mar. 27, 2003.

B. Dingel et al., "Speckle Reduction with Virutal Incoherent Laser Illumination Using A Microfiber Array", Optik 94, at 132 (1993).

U.S. Office Action mailed Aug. 2, 2005, from U.S. Appl. No. 10/688,086.

* cited by examiner

VARIABLE ILLUMINATOR AND SPECKLE BUSTER APPARATUS

CROSS REFERENCE TO RELATED PATENT APPLICATION

This application claims priority of U.S. Provisional Patent Application No. 60/643,618, entitled VARIABLE ILLUMINATOR AND SPECKLE BUSTER APPARATUS, filed 12 Jan. 2005 by Damon F. Kvamme, which application is incorporated herein by reference in its entirety for all purposes.

FIELD OF THE INVENTION

This invention pertains to apparatus and methods for illuminating a specimen, such as a photomask, with partially incoherent laser light, for example during an inspection procedure. Specifically, the invention pertains to apparatus and methods for providing variable illumination while reducing effects caused by incident light coherence.

BACKGROUND

Generally, the industry of semiconductor manufacturing involves highly complex techniques for fabricating integrating circuits using semiconductor materials. Due to the large scale of circuit integration and the decreasing size of semiconductor devices, decreasingly small defects, such as a particle, can cause the devices to fail. Defect inspection is therefore critical to maintain quality control. Since the inspection methods are an integral and significant part of the manufacturing process, the semiconductor industry is constantly seeking more accurate and efficient testing methods.

Various inspection systems are used within the semiconductor industry to detect defects on a semiconductor device or wafer. One type of inspection tool is an optical inspection system. In optical inspection systems, one or more radiation beams are directed towards the semiconductor wafer or photomask and a reflected and/or scattered beam is then detected. The detected beam is used to then generate a detected electrical signal or an image, and such signal or image is then analyzed to determine whether defects are present on the wafer.

Lasers are used as light sources in many inspection systems to measure defects on photomasks or wafers. Lasers provide light with high intensity to provide ample sample illumination and can provide a collimated beam of light that can be directed easily through lenses and toward the sample. Additionally, laser sources with a short wavelength may be advantageously used for examining relatively small feature sizes.

One of the downsides, however, of using lasers is that the high spatial and temporal coherence of laser light can cause constructive and destructive interference patterns when viewing images of the sample being inspected. The images can be obscured by interference effects such as the edge ringing evident in a coherent image, which can hide detail near any edges in the image, or by speckle, which appears as a nonuniform illumination of the object being imaged. Comprehensive discussions about interference effects such as edge ringing and speckle phenomena can be found in "Fourier Optics", by J. W. Goodman, McGraw-Hill, and "Statistical Optics", also by J. W. Goodman, Wiley-Interscience.

These deleterious image effects can be improved by reducing the spatial coherence of the laser light that is used to illuminate the object being imaged. One conventional technique of providing partially incoherent laser light involves the use of a rotating diffuser. A rotating diffuser typically consists of a rotating ground-glass screen that is introduced into the path of the laser beam before it reaches the object being imaged. The rotating diffuser introduces random phase variations into the incident laser beam, thereby introducing spatial incoherence to the beam. As the diffuser rotates, a detector can collect images of the object from independent views or perspectives. The detector, in turn, can integrate or add the independent inspection views to effectively synthesize a uniform illumination of the object being imaged that is relatively free of speckle.

In certain applications, it is frequently required that the inspection system have configurable illumination and imaging designs. The illumination and imaging configuration will be set to optimize the capture of different characteristics of defects or defect types. That is, different illumination and imaging configurations are more suitable for different types of defect inspections. Two broad categories of inspection configurations include bright field and dark field inspection. In general, the illumination and collection beam profiles are adjusted to achieve different inspection modes. In other words, different portions or angles of the incident or collection beam are blocked or transmitted.

For a dark field inspection, a portion of the illumination beam profile is typically blocked so that only a portion of the available illumination, for example a ring of illumination, is passed through to the wafer. A corresponding portion of the collection beam profile is then blocked so that only scattered light is collected. That is, blocked portions of the illumination beam correspond to unblocked portions of the collection beam, while unblocked portions of the illumination beam correspond to blocked portions of the collection beam. Both the illumination and the collection adjustments implement binary masks. That is, portions of the beam are totally blocked by the mask, while other portions of the beam pass unimpeded through the mask. Other types of illumination profiles include annular, dipole, and quadrapole illumination profiles. In general, specific illumination profiles are used to enhance or optimize the imaging quality of specific types of features. By way of examples, a quadrapole illumination profile may be used to image a field of contacts, while a dipole profile may be used to image a vertical line.

Unfortunately, a rotating diffuser typically produces a scattered pattern that has a Gaussian or non-uniform shape at the system pupil. For instance, the intensity may be significantly greater at the pupil center than at the pupil edges. Consequently, it would be difficult to implement various illumination profiles with a rotating diffuser, as opposed to a flatter illumination profile. Additionally, when blocking any of the center portion of the Gaussian shaped profile, a significant amount of light is unused. Thus, this type of arrangement does not efficiently utilize the light.

There is a need for improved and light-efficient mechanisms that provide varying illumination patterns in an incident beam directed at a sample, while reducing effects caused by coherence, such as speckle effect, in the incident beam.

SUMMARY

Accordingly, mechanisms for illuminating a sample, such as a semiconductor wafer or reticle, are provided. These mechanisms provide variable illumination profiles while reducing coherence effects, such as speckle, e.g., during such illumination of the sample. In one embodiment, an apparatus for illuminating a sample is disclosed. This apparatus includes a laser that outputs an incident laser beam towards a sample and a first diffractive element having a plurality of diffraction pattern portions. The first diffractive element is movable so that each of its diffraction pattern portions can be selectively positioned in the incident beam's path and the diffraction pattern portions of the first diffractive element are designed to cause the incident beam to have different spatial illumination profiles at a pupil plane of the incident beam while reducing effects caused by the incident beam's coherence. The apparatus further includes an illumination profile element configured to spatially distribute light at an illumination plane of the incident beam and a plurality of illumination optical elements for directing the incident beam towards the sample.

In a specific implementation, each of the first diffractive element's diffractive pattern portions is an annular section that is selectively positionable in the incident beam's path and the first diffractive element is rotatable so as to position different cells of its selected annular section into the incident beam's path to thereby reduce effects caused by the incident beam's coherence. In a further aspect, the different illumination profiles caused by the first diffractive element include at least two profiles selected from the following: an annular profile, a quadrapole profile, a dipole profile, a flat profile across a radius of the pupil, a Gaussian shaped profile across a radius of the pupil, and a circular shaped profile.

In one implementation, the cells of each annular section of the first diffractive element are disposed and oriented in a rectilinear pattern and the different illumination profiles caused by the first diffractive element only include profiles that are rotationally symmetric. In another embodiment, the cells of each annular section of the first diffractive element are disposed and oriented in a radial pattern and the different illumination profiles caused by the first diffractive element include profiles that are not rotationally symmetric.

In one aspect, the illumination profile element has a fixed position to thereby form a single illumination profile at the illumination plane. In another aspect, the illumination profile element is movable so as to form a plurality of different selectable illumination profiles at the illumination plane. In a particular embodiment, the illumination profile element has a plurality of aperture portions that are each selectively positionable in the path of the incident beam and each aperture portion causes a different illumination profile at the illumination plane when it is positioned in the path of the incident beam. For example, the illumination profiles caused by the illumination profile element include at least two profiles selected from the following: a square shape, a circular shape, and a rectangular shape.

In another implementation, the illumination profile element takes the form of a second diffractive element having a plurality of diffraction pattern portions, and the second diffractive element is movable so that each of its diffraction pattern portions are selectively positionable in the incident beam's path. The diffraction patterns of the second diffractive element are designed to cause the incident beam to have different spatial illumination patterns at the incident beam's illumination plane and to reduce effects caused by the incident beam's coherence. In one aspect, the effects caused by the incident beam's coherence include a speckle effect. In a further implementation, the first and second diffractive elements are rotatable so as to position different sub-portions of their respective selected diffraction pattern portions into the incident beam's path to thereby decrease the incident beam's coherence.

In a specific aspect, each of the first diffractive element's diffractive pattern portions is an annular section that is selectively positionable in the incident beam's path to cause different illumination profiles at the pupil, and the first diffractive element is rotatable so as to position different cells of its selected annular section into the incident beam's path to thereby reduce effects caused by the incident beam's coherence. Additionally, each of the illumination profile element's diffractive pattern portions is an annular section that is selectively positionable in the incident beam's path to cause different illumination profiles at the illumination plane, and the illumination profile element is rotatable so as to position different cells of its selected annular section into the incident beam's path to thereby reduce effects caused by the incident beam's coherence.

In one implementation, the first diffractive element is positioned between the laser and the illumination profile element, and the illumination profile element is positioned at a pupil plane of the incident beam and between the first diffractive element and the sample. In another implementation, the illumination profile element is positioned at a pupil plane of the incident beam and between the laser and the first diffractive element, and the first diffractive element is positioned at an illumination plane of the incident beam and between the illumination profile element and the sample.

In another aspect the invention pertains to an apparatus for inspecting a sample. The apparatus includes any of the above described elements, as well as a detector for outputting a signal or an image based on a detected output beam and a plurality of detection optical elements for directing a output beam emanating from the sample in response to the incident beam towards the detector. This inspection apparatus further includes an analyzer arranged to analyze the output signal or image and determine whether the sample has defects.

In an illumination method, an incident laser beam is directed from a laser through a first diffractive element and an illumination profile towards a sample. The first diffractive element includes a plurality of diffraction pattern portions and the diffraction pattern portions of the first diffractive element are designed to cause the incident beam to have different spatial illumination profiles at a pupil plane of the incident beam while reducing effects caused by the incident beam's coherence. The illumination profile element is configured to spatially distribute light at an illumination plane of the incident beam. The method further includes an operation for moving the first diffractive element so that a selected one of the diffraction pattern portions is selectively positioned in the incident beam's path to thereby cause the first diffractive element to form a selected one of the illumination profiles at the pupil plane.

In a specific aspect, each of the first diffractive element's diffractive pattern portions is an annular section that is selectively positionable in the incident beam's path and the first diffractive element is rotatable so as to position different cells of its selected annular section into the incident beam's path to thereby reduce effects caused by the incident beam's coherence, and the method includes an operation for rotating the first diffractive element. In another aspect, the illumination profile element has a plurality of aperture portions that are each selectively positionable in the path of the incident beam and each aperture portion causes a different illumination profile at the illumination plane when it is positioned in the path of the incident beam, and the method further includes an operation for moving the illumination profile element so as to selectively position a selected one of the aperture portions in the path of the incident beam to cause a selected one of the illumination profiles to be formed at the illumination plane.

Embodiments of the present invention flexibly provide variable illumination profiles at the pupil while reducing effects caused by the incident light coherence, such as the speckle effect. In other words, a mechanism for spatially distributing light at the pupil with different selectable profiles is provided. This arrangement allows one to select an illumination profile that will optimize illumination of the sample and thereby optimize detection of features on such sample. Embodiments that utilize a rotating diffuser to provide variable illumination profiles and reduce speckle also efficiently utilized the provided incident light. Embodiments of the present invention also spatially distribute light at the illumination plane of the incident beam, and some embodiments provide variable distribution at the illumination plane to provide flexibility in object light distribution. For example, the spatial distribution at the object may be tailored to specific types of detector shapes to thereby maximize light collection efficiency.

These and other features of the present invention will be presented in more detail in the following specification of the invention and the accompanying figures which illustrate by way of example the principles of the invention.

BRIEF DESCRIPTION OF THE DRAWINGS

The following detailed description can be more fully understood when considered in conjunction with the drawings in which.

DETAILED DESCRIPTION OF A SPECIFIC EMBODIMENTS

Reference will now be made in detail to specific embodiments of the invention. Examples of some of these embodiments are illustrated in the accompanying drawings. While the invention will be described in conjunction with these specific embodiments, it will be understood that it is not intended to limit the invention to these particular embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention. Principles of the invention regarding the optics involved will also be described. These principles are discussed to clarify the invention and are not meant to limit the invention to particular theories.

As used herein, "specimen" will be used to describe any object that can be illuminated or inspected using the present invention. The specimen is preferably a mask, such as a photomask, reticle or wafer used in integrated circuit manufacturing processes. However, it can be appreciated by those skilled in the art that a specimen can include other types of objects that are to be inspected for small defects and inconsistencies. The present invention is particularly useful for inspecting defects, such as particle defects, mask defects or wafer defects due to: pattern writing errors, critical dimension errors, bridging defects, and phase defects, on or in a specimen. The invention is not, however, limited to any particular types of defects or inconsistencies in or on the specimen. Additionally, embodiments of the present invention are not limited to being implemented within inspection systems and may be implemented within any suitable imaging apparatus for illuminating a specimen.

Figure 1:
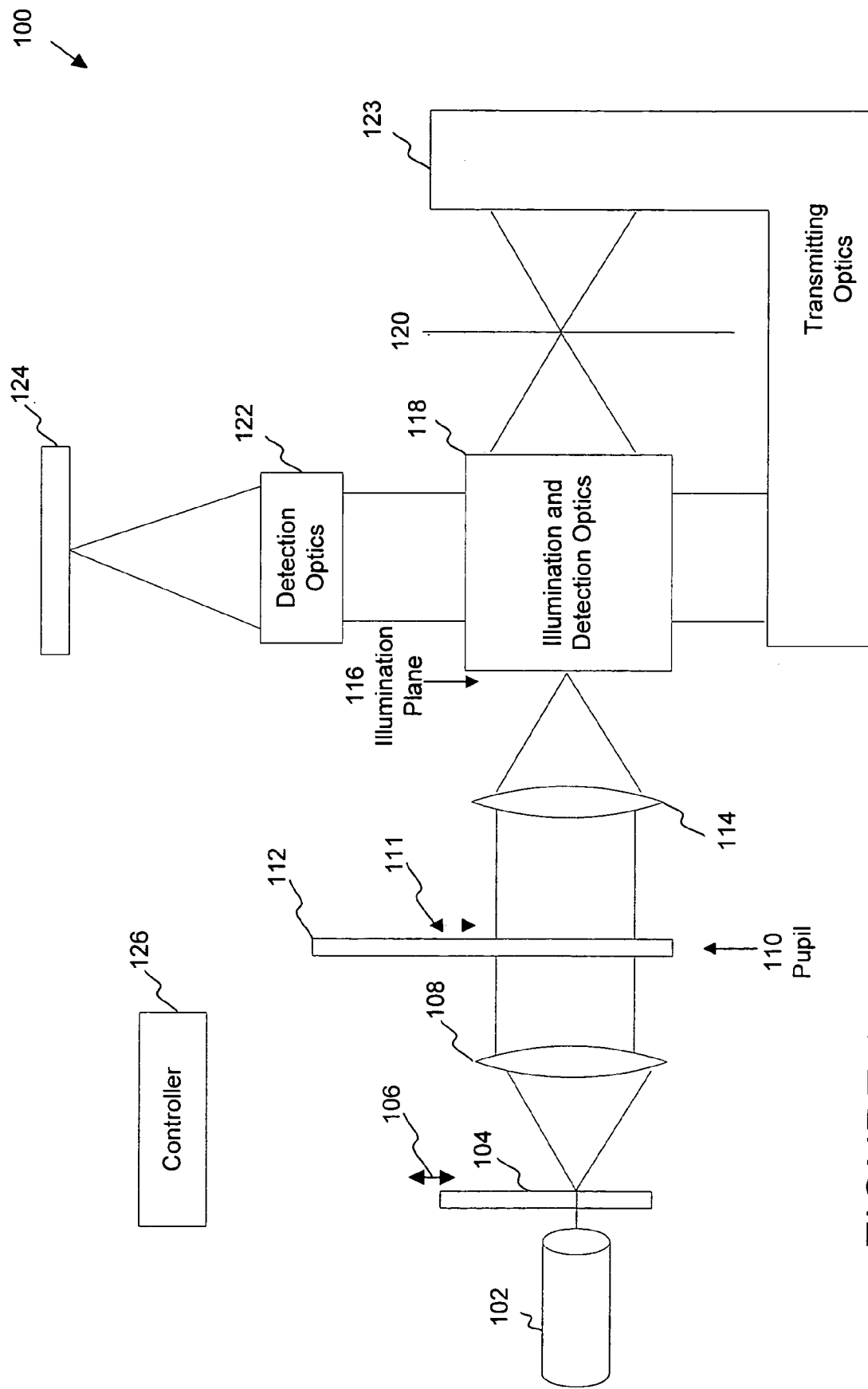
FIG. 1 is a diagrammatic representation of an inspection system in accordance with one embodiment of the present invention.

FIG. 1 is a diagrammatic representation of an inspection system 100 in accordance with one embodiment of the present invention. As shown, the system includes illumination components for directing an incident beam towards sample 120 and detection components for detecting output light emanating from the sample in response to the incident beam as well as features on the sample. In one inspection application, this output light may be analyzed to determine whether the sample has defects. For instance the output light intensity from a particular area of the sample may be compared to another area of the sample that is designed to be identical to the first area. Any significant differences between the intensities patterns output from the two areas may indicate a defect in either the first or second area.

In the inspection systems described herein, any suitable lens arrangement may generally be used to direct the incident beams towards the sample and direct the output beams emanating from the sample towards a detector. The output beams may be diffracted, reflected or scattered from the sample or transmitted through the sample. Likewise, any suitable detector type or number of detection elements may be used to receive the output beams and provide an image or a signal based on the characteristics (e.g., intensity) of the received output beams.

Details of the illumination components will now be described. Descriptions of some of the optical components of the embodiment described below, as well as other components of optical systems that may designed in accordance with the present invention, can be found, for example, in Warren J. Smith, Modern Optical Engineering, 2nd edition, McGraw-Hill, Inc., 1990, which is incorporated herein by reference.

Laser 102 provides an incident laser beam, which is temporally and spatially coherent. Laser 102 is preferably a continuous wave laser, although a pulsed laser may also be used. The wavelength of light that the laser emits will depend upon the application of the inspection system. For example, in typical photomask inspection applications, lasers that emit ultraviolet light or shorter wavelengths are preferable. For example, two standard ultraviolet lasers emit light with wavelengths at 257 nm and 193 nm. Note, however, that the invention does not depend on the wavelength of light emitted by the laser and any wavelength may be used.

Once emitted from laser 102, the incident laser beam may immediately pass through a first diffractive element 104 that is designed to provide a plurality of different selectable illumination profiles at the incident beam's pupil plane while reducing the effects caused by the incident beam coherence, e.g., speckle. The first diffractive element 104 is preferably placed proximate to the laser 102 so that the incident beam has a relatively small beam size. This placement allows the first diffractive element to include a plurality of different diffraction pattern portions that are selectively movable in the incident beam's path while minimizing the first diffractive element's size. For example, first diffractive element 104 is movable in a linear direction 106. In a specific implementation, the first diffractive element 104 is also a rotating diffuser designed to reduce speckle. Several embodiments of a first diffractive element for providing variable illumination profiles at the pupil are described further below.

After passing through the first diffractive element 104, the incident beam passes through a lens element 108 that is configured to form pupil 110 at an illumination profile element 112 that is designed to spatially distribute light at an illumination plane of the incident beam. The illumination profile element 112 may also be movable in a linear direction 111 so as to provide variable illumination profiles at the illumination plane. In an alternative embodiment, the illumination profile element 112 may be fixably positioned to provide a single illumination profile at the illumination plane. In other embodiments, the illumination profile element 112 may take the form of a second rotating diffuser designed to reduce speckle. Several embodiments of an illumination profile element for providing one or more illumination profiles at the illumination plane are described further below.

The relative positions of the first diffractive element 104 and illumination profile element 112 are interchangeable. In the illustration, the first diffractive element 104 is positioned between the laser 102 and the illumination profile element 112, and the illumination profile element 112 is positioned between the first diffractive element 104 and the sample 120. Alternatively, the illumination profile element 112 may be positioned between the laser 102 and the first diffractive element 104, and the first diffractive element 104 may be positioned between the illumination profile element 112 and the sample 120. For example, the first diffractive element 104 may be positioned at illumination plane 116 of FIG. 1. In general, the first diffractive element 104 is positioned so as to distribute light at any one of the pupil planes present within the incident beam's path. Similarly, the illumination profile element 112 is positioned so as to distribute light at any one of the illumination planes present within the incident beam's path.

As shown, the incident beam is also passed through an illumination and detection optics block 118 to sample 120. The illumination and detection optics block 118 is configured to further direct the incident beam towards the sample and to direct an output beam emanating from the sample in response to such incident beam towards detection optics 122. The system may also include transmitting optics 123 for directing light transmitted through the sample towards detection optics 122. Detection optics 122 are configured to direct the output beam towards detector 124, and detector 124 is generally configured to generate a detection signal or image that corresponds to the detected output beam.

Suitable detectors can encompass a wide range of light detector elements known to persons of ordinary skill in the art. Such elements can include, without limitation, photomultiplier tubes, photodiodes, CCD's, and arrays of such structures. Also, TDI (time domain integration) sensor arrays may also be used. Information obtained by such detector elements is typically converted to electrical (or in some cases optical) signals that are transmitted to an image processor. The image processor can conduct a wide range of operations on signals received from the detector element. Such operations include, but are not limited to, data processing and signal and data analysis as well as a myriad of other operations known to persons having ordinary skill in the art. The image processor can include, without limitation, microprocessors, computers, DSP's, ASIC's, memory, and a variety of other related electronic elements. Commonly, such image processors include signal processing elements and/or modules that can conduct analysis of the detected images of the surface to detect, locate, and quantify defects.

The system 100 may include various other elements (not shown) for directing the incident beam from the laser 102 towards the sample 120 and for directing the output beam from the sample 120 towards the detector 124. For instance, as it exits the laser 102, the incident beam may be directed toward a beam expander, which magnifies the laser beam thereby scaling the laser beam width to appropriately pass through the lens and aperture assemblies of the inspection system. Magnifying the incident laser beam causes it to diverge. Therefore, incident laser beam may then be directed toward a lens which refocuses the laser beam. The incident beam may then pass or reflect from any suitable number and type of lenses, in addition to the first diffractive element 106 and illumination profile element 112.

The illumination optics (e.g., 118) may include a tunnel for mixing the light to evenly distribute the light after it has passed through first diffractive element 104 and illumination profile element 112. The illumination and detection optics block 118 may include this light tunnel, as well as elements for directing the incident beam towards the sample and directing any output beams from the sample towards the detector 124. For example, the incident beam may pass through a splitter and any scattered or reflected output beams from the sample may be reflected off this same splitter towards detection optics 122 and detector 124. The illumination block 118 may also include a relay lens for relaying the Fourier plane of the output beam towards another aperture that is configured to spatially filter portions of the output beam. In one implementation, the light from repeating features is filtered from the output beam so as to emphasis defects on the sample.

The inspection system also includes a controller 126 in the form of any suitable combination of software and hardware (e.g., such as one or more memory and processors programmed to operate the system components and analyze data from such components). The controller 126 is generally configured to control various components of the inspection system 100. For instance, the controller 126 may control activation of the illumination source 102, movement of the first diffractive element, movement of the illumination profile element, etc. The controller 110 may also receive the image or signal generated by the detector 124 and be configured to analyze the resulting image or signal to determine whether defects are present on the sample, characterize defects present on the sample, or otherwise characterize the sample. For instance, an image of the sample may be compared to a reference image that is obtained from another die, an adjacent area, or a design database. This comparison may result in a discrepancy between the two images which is characterized as a defect when the difference is significant (e.g., exceeds a predetermined threshold).

The first diffractive element 104 and illumination profile element 112 may each take any suitable form for spatially distributing light at the pupil and illumination plane, respectively, as well as reducing effects caused by the incident light coherence (at least in the first diffractive element 104). One or both elements may take the form of a diffractive element having a plurality of diffraction pattern sections imprinted thereon. Each diffraction pattern section is designed to cause a different illumination profile to be formed when selectively positioned across the incident beam path (e.g., by movement in linear direction 106 or 111 shown in FIG. 1). Each diffraction pattern section is also preferably configured to reduce coherence effects.

Figure 2A:
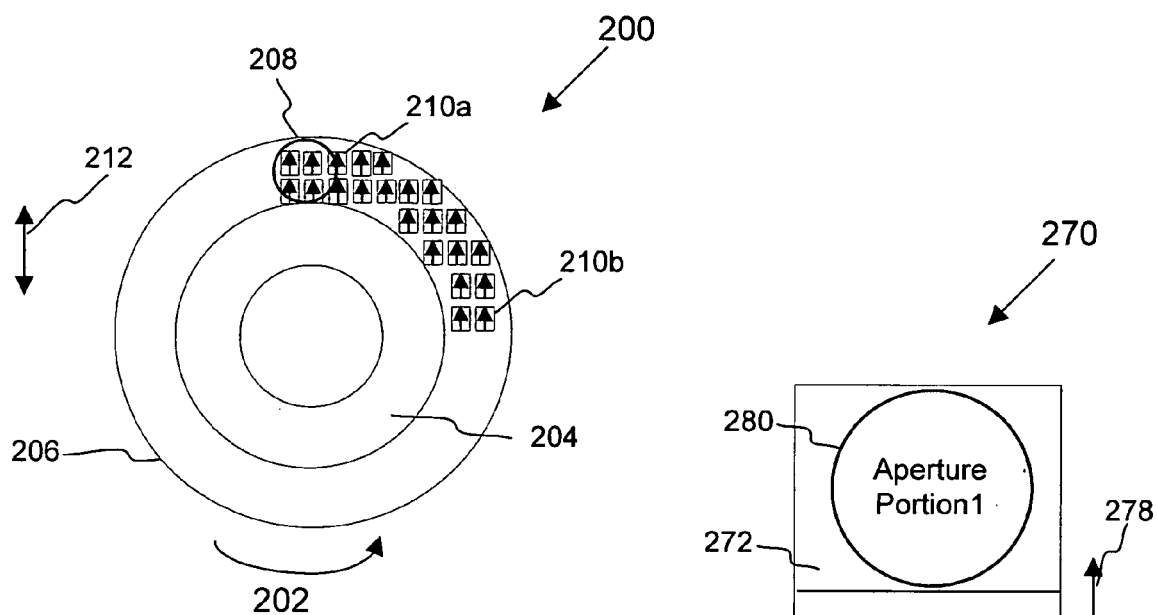
FIG. 2A illustrates a rotating diffuser in accordance with a first embodiment of the present invention.

In one implementation, the first diffractive element 104 takes the form of a rotating diffuser. In alternative embodiments, the illumination profile element 112 also takes the form of a rotating diffuser. FIG. 2A illustrates a rotating diffuser 200 in accordance with a first embodiment of the present invention. As shown, the rotating diffuser 200 is divided into a plurality of annular sections, such as annular sections 204 and 206. Each annular section corresponds to a different illumination profile that is selectable by moving the diffuser in direction 212 with respect to the incident beam 208. For example, when the incident beam cross section 208 passes through annular section 204 (not shown), a first illumination profile is formed at the pupil, while when the incident beam passes through annular section 206 (shown), a second illumination profile is formed at the pupil. A separate rotating diffuser may also be designed to produce different illumination profiles at the illumination plane.

Each annular section also contains a plurality of cells (only a few are shown so as to not obscure the invention). The cells are preferably arranged and sized so that the incident beam passes substantially within a plurality of cells. The cells are designed so as to reduce effects from the incident beam's coherence, e.g., speckle, when the diffuser is rotated in direction 202 by way of example. To reduce speckle, the cells introduce random phase variations into the incident beam, thereby introducing spatial incoherence in the incident beam.

As the diffuser is rotated, a set of cells of the selected annular section (e.g., 206) is passed over beam path 208. In this embodiment, the cells are disposed and oriented in a rectilinear pattern. As shown, the cells each show an arrow that is pointed up which corresponds to the pattern in each cell being oriented the same way with respect to the x and y axis. For instance, cell 210a is oriented in a different manner than cell 210b as they each pass through beam 208. In this embodiment, the illumination profiles produced by this diffuser 200 only include profiles that are rotationally symmetric (e.g., an annular or circular illumination profile) so that different cell orientations with respect to the beam 208 will not produce different profiles.

Figure 2C:
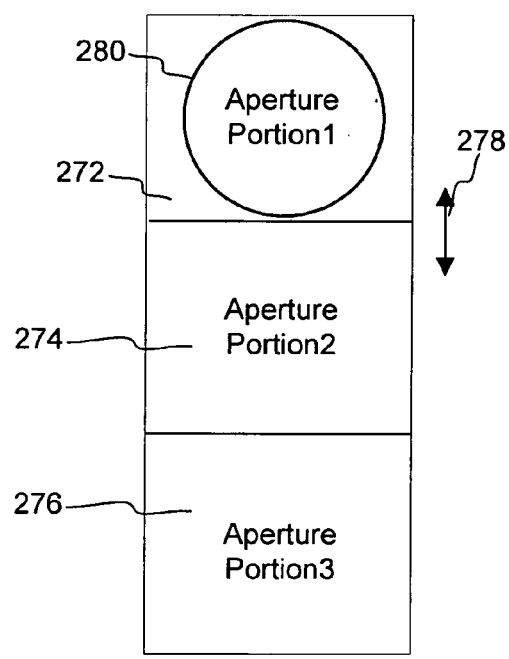
FIG. 2C illustrates an indexable illumination profile element in accordance with an alternative embodiment of the present invention.
Figure 2B:
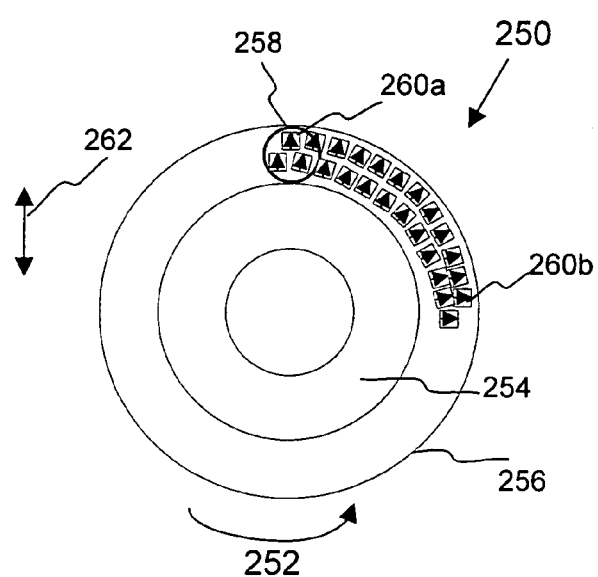
FIG. 2B illustrates a rotating diffuser in accordance with a second embodiment of the present invention.

FIG. 2B illustrates a rotating diffuser 250 in accordance with a second embodiment of the present invention. This rotating diffuser includes a plurality of annular sections (e.g., 254 and 256) that are movable along direction 262 so that a selected annular section is positioned in beam path 258. The rotating diffuser also rotates, for example, in direction 252. Each annular section also includes a number of cells. However, the cells are disposed and oriented along a radial direction. That is, as each cell rotates to the beam path position 258, it has a substantially same orientation with respect to the beam 258. For example, cell 260a will have a same orientation with respect to beam path 258 when it is positioned adjacent to such beam as when cell 260b is positioned adjacent to the beam. In this embodiment, the illumination profiles produced by this diffuser 250 can include profiles that are not rotationally symmetric since different cell orientations are not present with respect to the beam 208 and will not result in diverse illumination profiles.

Figure 3A:
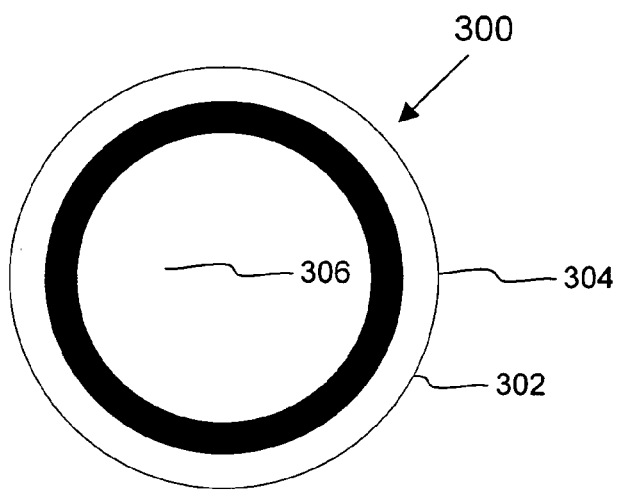
FIGS. 3A through 3F represent different illumination profiles that can be produced at the pupil plane by embodiments of the present invention.
Figure 3B:
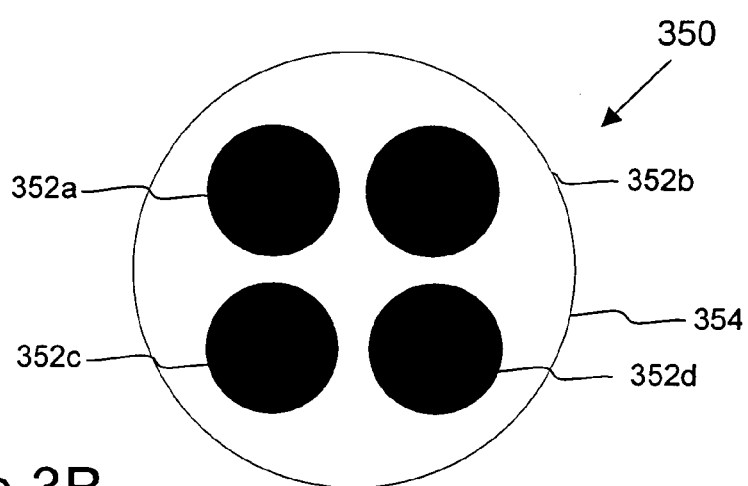
Figure 3C:
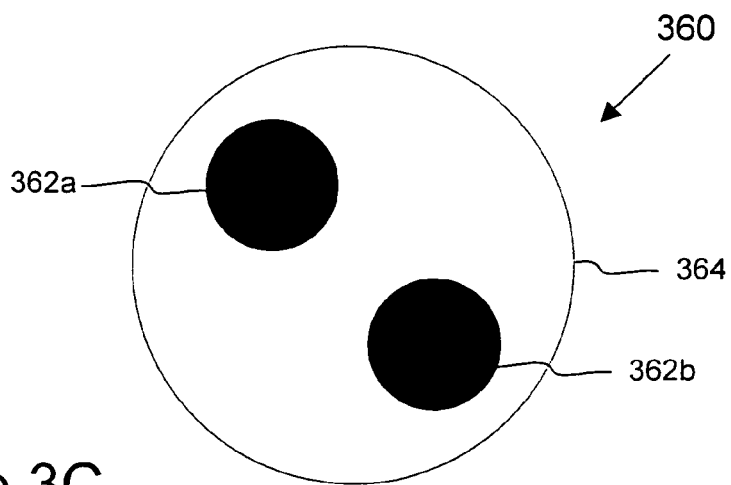
Figure 3D:
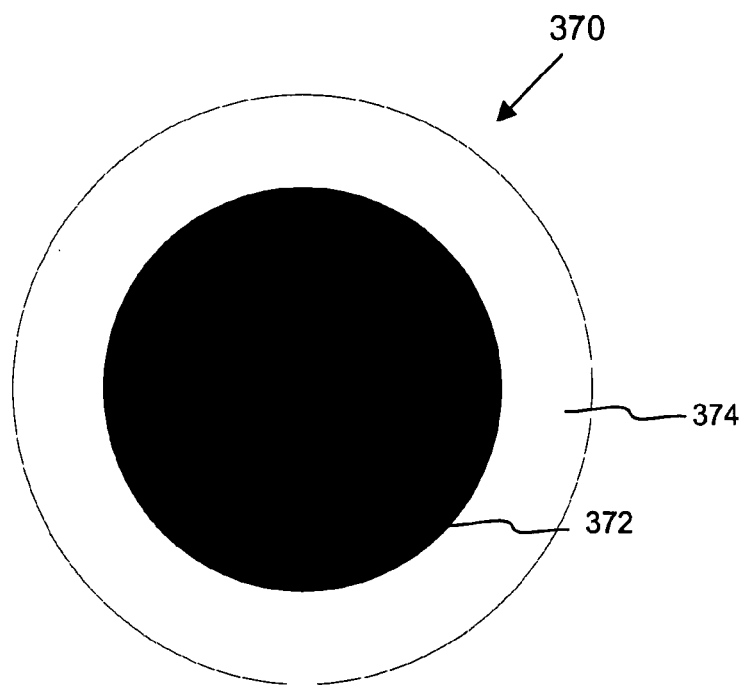
Figure 3E:
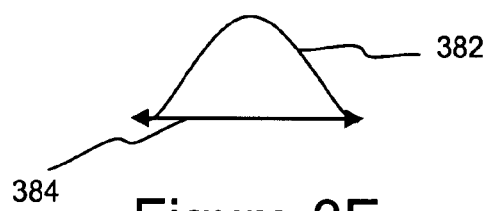
Figure 3F:
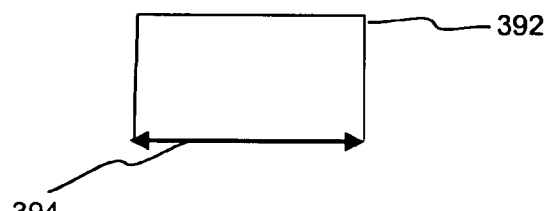

FIGS. 3A through 3F represent different illumination profiles that can be produced at the pupil plane by embodiments of the present invention, such as the rotating diffuser of FIG. 2A or 2B. FIGS. 3A through 3D show two dimensional intensity distributions in the pupil plane, while FIGS. 3E and 3F are simple cross-sections of rotationally symmetric intensity distributions. For example, the incident beam cross section at the pupil plane is represented by the dark sections. FIG. 3A shows pupil plane 300 with an annular illumination profile for the beam. That is, only an annular portion 302 of the incident beam is generated at the pupil 300, while portions 304 and 306 of the incident beam are not. FIG. 3B illustrates pupil plane 350 with a quadrapole illumination profile for the incident beam. That is, only quadrapole portions 352a through 352d of the incident beam are generated at the pupil 350, while portion 354 of the incident beam is not.

FIG. 3C illustrates pupil plane 360 with a dipole illumination profile for the incident beam. That is, only dipole portions 362a and 362b of the incident beam are generated at the pupil 350, while portion 364 of the incident beam is not. FIG. 3D illustrates pupil plane 370 with a circular shaped illumination profile for the incident beam. That is, only circular shaped portion 372 of the incident beam is generated at the pupil 350, while portion 374 of the incident beam is not.

Varying illumination intensity profiles may also be produced at the pupil plane. As shown in FIG. 3E, a Gaussian shaped illumination profile 382 may be formed across the beam radius 384. In the example of FIG. 3F, a flat intensity illumination profile 392 may be formed across the beam radius 394.

A rotating diffuser may be designed with annular sections to selectively produce any combination of the above described illumination profiles at the pupil plane as well as any other suitable profiles. That is, the present invention is not limited to the illumination profiles described herein. A rotating diffuser may also be designed with annular sections to selectively produce any combination of illumination profile at the illumination plane. In either case, the annular sections and cells located therein may also be designed to reduce effects caused by incident light coherence, such as speckle. Suitable rotating diffusers are available from Digital Optics Corporation of Charlotte, N.C.

Figure 4A:
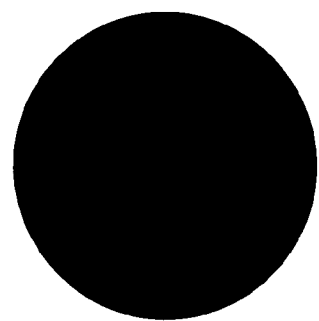
FIGS. 4A through 4C represent different illumination profiles that can be produced at the illumination plane by embodiments of the present invention.
Figure 4B:
Figure 4C:

FIGS. 4A through 4C represent different illumination profiles that can be produced at the illumination plane by embodiments of the present invention. FIG. 4A shows a circular illumination profile at the illumination plane; FIG. 4B shows a rectangular illumination profile at the illumination plane; and FIG. 4C shows a square illumination profile at the illumination plane. Of course, other types of illuminations profiles may be generated with the present invention.

The above described rotating diffuser may be designed to (i) spatially distribute light at the pupil plane and reduce effects caused by the incident beam coherence or (ii) spatially distribute light at the illumination plane and reduce effects caused by the incident beam coherence or both. That is, a rotating diffuser may be used for the first diffractive element 104 and/or illumination profile element 112 of FIG. 1. Alternatively, the illumination profile element 112 may be fixed to produce a single illumination pattern at the illumination plane. In another embodiment, the illumination profile element 112 can take the form of an element that is movable in a linear direction in the pupil plane.

FIG. 2C illustrates an indexable illumination profile element 270 for distributing light at the illumination plane in accordance with an alternative embodiment of the present invention. As shown, the illumination profile element 270 is movable along direction 278 so as to selectively position a selected one of a plurality of aperture portions in beam path 280. For example, aperture portion 272 is shown as being positioned within beam path 280. However, the illumination profile element 270 may be moved so as to place aperture portion 274 or 276 in beam path 280. Each aperture portion produces a different illumination profile at the illumination plane when the illumination profile element 270 is positioned in a pupil plane of the incident beam.

Figure 5:
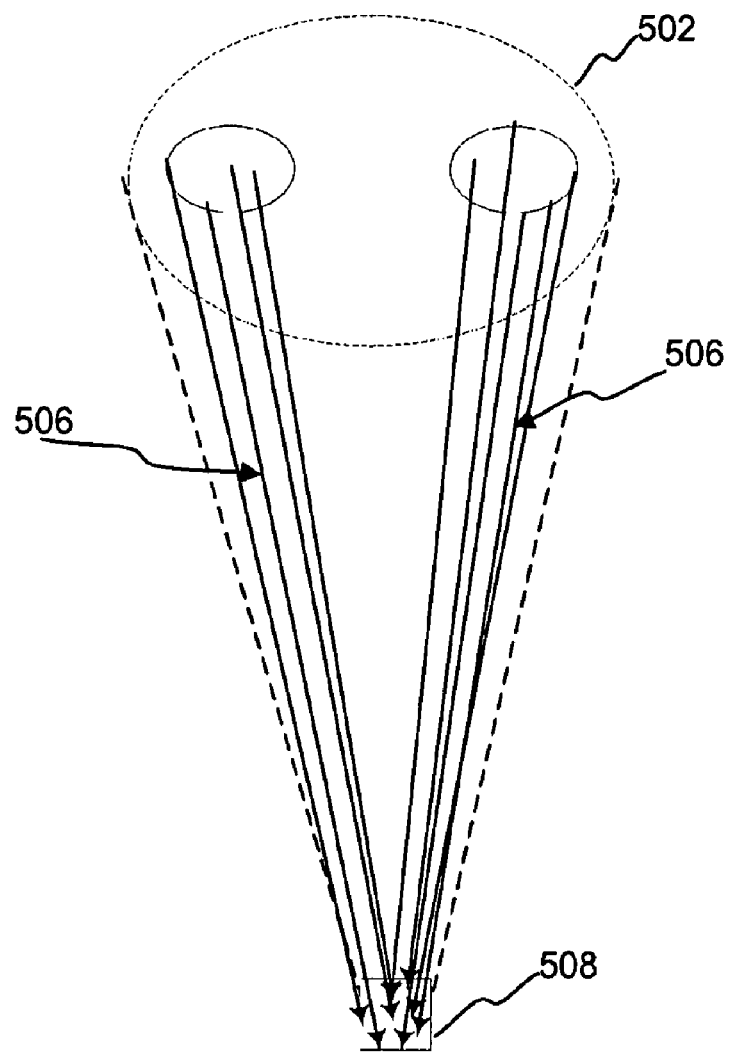
FIG. 5 is a diagrammatic representation of spatially distributing light at both the pupil and illumination plane of the incident light in accordance with one embodiment of the present invention.

FIG. 5 is a diagrammatic representation of spatially distributing light at both the pupil and illumination plane of the incident light in accordance with one embodiment of the present invention. In the present invention, a diffractive element is configured to spatially distribute light at the pupil plane, while a separate element is used to spatially distribute light at the illumination plane. As shown, specific incident beam portions 506 pass through pupil plane 502. Each position in the pupil plane 502 corresponds to a specific incident angle of one of the specific incident beam portions 506 that passes through the illumination plane 508. In this example, the incident beam portions 506 are also spatially distributed into a square shape 508 in the illumination plane.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, the specimen may be any substance or object that is suitable for laser inspection or review, such as a semiconductor wafer or reticle. By way of a final example, the present invention may be useful in inspecting or reviewing photomasks, which are being designed with smaller and smaller dimensions. Accordingly, the present embodiments are to be considered as illustrative and not restrictive, and the invention is not to be limited to the details given herein, but may be modified within the scope and equivalents of the appended claims.

What is claimed is:

1. An apparatus for illuminating a sample, comprising:
   a laser for outputting an incident laser beam towards the sample;
   a first diffractive element having a plurality of diffraction pattern portions, wherein the first diffractive element is movable so that each of its diffraction pattern portions is selectively positioned in the incident beam's path and the diffraction pattern portions of the first diffractive element are designed to cause the incident beam to have different spatial illumination profiles at a pupil plane of the incident beam while reducing effects caused by the incident beam's coherence, wherein the diffractive pattern portions are different annular sections of the first diffractive element and each annular section has a plurality of cells thereon and the annular sections are selectively positionable in the incident beam's path so as to provide the different spatial illumination profiles and the first diffractive element is rotatable so as to sequentially position different cells of its selected annular section into the incident beam's path during illumination of the sample to thereby introduce phase variations into the incident beam and reduce effects caused by the incident beam's coherence;
   an illumination profile element configured to spatially distribute light at an illumination plane of the incident beam; and
   a plurality of illumination optical elements for directing the incident beam towards the sample.

2. An apparatus as recited in claim 1, wherein the different illumination profiles caused by the first diffractive element include at least two profiles selected from a group consisting of an annular profile, a quadrapole profile, a dipole profile, a flat profile across a radius of the pupil, a Gaussian shaped profile across a radius of the pupil, and a circular shaped profile.

3. An apparatus as recited in claim 2, wherein the cells of each annular section of the first diffractive element are disposed and oriented in a rectilinear pattern and the different illumination profiles caused by the first diffractive element only include profiles that are rotationally symmetric.

4. An apparatus as recited in claim 2, wherein the cells of each annular section of the first diffractive element are disposed and oriented in a radial pattern and the different illumination profiles caused by the first diffractive element include profiles that are not rotationally symmetric.

5. An apparatus as recited in claim 2, wherein the illumination profile element has a fixed position to thereby form a single illumination profile at the illumination plane.

6. An apparatus as recited in claim 2, wherein the illumination profile element is movable so as form a plurality of different selectable illumination profiles at the illumination plane.

7. An apparatus as recited in claim 6, wherein the illumination profile element has a plurality of aperture portions that are each selectively positionable in the path of the incident beam and each aperture portion causes a different illumination profile at the illumination plane when it is positioned in the path of the incident beam.

8. An apparatus as recited in claim 7, wherein the illumination profiles caused by the illumination profile element include at least two profiles selected from a group consisting of a square shape, a circular shape, and a rectangular shape.

9. An apparatus as recited in claim 2, wherein the illumination profile element is in the form of a second diffractive element having a plurality of diffraction pattern portions, and the second diffractive element is movable so that each of its diffraction pattern portions are selectively positionable in the incident beam's path, wherein the diffraction patterns of the second diffractive element are designed to cause the incident beam to have different spatial illumination patterns at the incident beam's illumination plane and to reduce effects caused by the incident beam's coherence.

10. An apparatus as recited in claim 9, wherein the effects caused by the incident beam's coherence include a speckle effect.

11. An apparatus as recited in claim 10, wherein the first and second diffractive elements are rotatable so as to position different sub-portions of their respective selected diffraction pattern portions into the incident beam's path to thereby decrease the incident beam's coherence.

12. An apparatus as recited in claim 11, wherein
   each of the first diffractive element's diffractive pattern portions is an annular section that is selectively positionable in the incident beam's path to cause different illumination profiles at the pupil and the first diffractive element is rotatable so as to position different cells of its selected annular section into the incident beam's path to thereby reduce effects caused by the incident beam's coherence; and each of the illumination profile element's diffractive pattern portions is an annular section that is selectively positionable in the incident beam's path to cause different illumination profiles at the illumination plane and the illumination profile element is rotatable so as to position different cells of its selected annular section into the incident beam's path to thereby reduce effects caused by the incident beam's coherence.

13. An apparatus as recited in claim 12, wherein the different illumination profiles caused by the first diffractive element include at least two profiles selected from a group consisting of an annular profile, a quadrapole profile, a dipole profile, a flat profile across a radius of the pupil, a Gaussian shaped profile across a radius of the pupil, and a circular shaped profile, and the different illumination profiles caused by the illumination profile element include at least two profiles selected from a group consisting a square shape, a circular shape, and a rectangular shape.

14. An apparatus as recited in claim 13, wherein the cells of each annular section of the first diffractive element and the illumination profile element are disposed and oriented in a rectilinear pattern and the different illumination profiles caused by the first diffractive element only include profiles that are rotationally symmetric.

15. An apparatus as recited in claim 13, wherein the cells of each annular section of the first diffractive element and the illumination profile element are disposed and oriented in a radial pattern and the different illumination profiles caused by the first diffractive element include profiles that are not rotationally symmetric.

16. An apparatus as recited in claim 2, wherein the first diffractive element is positioned between the laser and the illumination profile element, and the illumination profile element is positioned at a pupil plane of the incident beam and between the first diffractive element and the sample.

17. An apparatus as recited in claim 2, wherein the illumination profile element is positioned at a pupil plane of the incident beam and between the laser and the first diffractive element, and the first diffractive element is positioned at an illumination plane of the incident beam and between the illumination profile element and the sample.

18. An apparatus for inspecting a sample, comprising an apparatus as recited in claim 2;

a detector for outputting an output signal or an image based on a detected output beam;

a plurality of detection optical elements for directing an output beam emanating from the sample in response to the incident beam towards the detector and an analyzer arranged to analyze the output signal or image and determine whether the sample has defects.

19. A method of inspecting a specimen comprising:

directing an incident laser beam from a laser through a first diffractive element and an illumination profile element towards a sample, wherein the first diffractive element includes a plurality of diffraction pattern portions and the diffraction pattern portions of the first diffractive element are designed to cause the incident beam to have different spatial illumination profiles at a pupil plane of the incident beam while reducing effects caused by the incident beam's coherence, wherein the illumination profile element is configured to spatially distribute light at an illumination plane of the incident beam; and moving the first diffractive element so that a selected one of the diffraction pattern portions is selectively positioned in the incident beam's path to thereby cause the first diffractive element to form a selected one of the illumination profiles at the pupil plane.

wherein the diffractive pattern portions are different annular sections of the first diffractive element and each annular section has a plurality of cells thereon and the annular sections are selectively positionable in the incident beam's path so as to provide the different spatial illumination profiles and the first diffractive element is rotatable so as to sequentially position different cells of its selected annular section into the incident beam's path during illumination of the sample to thereby introduce phase variations into the incident beam and reduce effects caused by the incident beam's coherence.

20. A method as recited in claim 19, wherein the illumination profile element has a plurality of aperture portions that are each selectively positionable in the path of the incident beam and each aperture portion causes a different illumination profile at the illumination plane when it is positioned in the path of the incident beam, the method comprising moving the illumination profile element so as to selectively position a selected one of the aperture portions in the path of the incident beam to cause a selected one of the illumination profiles to be formed at the illumination plane.

\* \* \* \* \*